US005438985A

United States Patent [19]
Essen-Moller

[11] Patent Number: 5,438,985
[45] Date of Patent: Aug. 8, 1995

[54] AMBULATORY RECORDING OF THE PRESENCE AND ACTIVITY OF SUBSTANCES IN GASTRO-INTESTINAL COMPARTMENTS

[75] Inventor: Anders Essen-Moller, Stockholm, Sweden

[73] Assignee: Synectics Medical, Incorporated, Irving, Tex.

[21] Appl. No.: 8,137

[22] Filed: Jan. 25, 1993

[51] Int. Cl.⁶ .............................................. A61B 5/00
[52] U.S. Cl. ................................... 128/633; 128/635; 128/665
[58] Field of Search .............................. 128/632-635, 128/637, 664-666, 780

[56] References Cited

U.S. PATENT DOCUMENTS

| | | |
|---|---|---|
| 2,162,656 | 6/1939 | Warrington . |
| 2,168,867 | 8/1939 | George, 3rd . |
| 2,857,915 | 10/1958 | Sheridan . |
| 3,373,735 | 3/1968 | Gallagher . |
| 3,480,003 | 11/1969 | Crites . |

(List continued on next page.)

FOREIGN PATENT DOCUMENTS

| | | | |
|---|---|---|---|
| 6673558 | 3/1983 | European Pat. Off. ............. | 128/634 |
| 0080680 | 6/1983 | European Pat. Off. . | |
| 0241644 | 10/1987 | European Pat. Off. . | |
| 0356603 | 11/1993 | European Pat. Off. . | |
| 2162656 | 6/1973 | Germany . | |
| 2453630 | 11/1980 | Germany . | |
| 3140265 | 4/1983 | Germany . | |
| 221635 | 5/1985 | Germany . | |
| 3523987 | 1/1987 | Germany . | |
| 4921789 | 2/1974 | Japan ................................. | 128/635 |
| 7707275 | 1/1979 | Netherlands . | |
| 178028 | 11/1966 | U.S.S.R. . | |

OTHER PUBLICATIONS

Assorted promotional material by Synetics Medical, Inc.
Butcher et al., Digestion, 1992, vol. 53, pp. 142-148, "Use of an Ammonia Electrode for Rapid Quantification of *Helicobacter pylori* Urease: Its use in the Endoscopy Room and in the . . . ".
"Clinical relevance of ambulatory 24-hour . . . ", Vogten, et al., 1987, pp. 21-31 in Netherlands Journal of Medecine.
"Computerized Axial Manometry of the Esophagus", Bombeck, et al. in Annals of Surgery, vol. 206, No. 4, pp. 465-472, Oct. 1987.
"The laser motility sensor for long-term study of intra--esophageal pressure", Schneider et al., in Primary Motility Disorder of the Esophagus, Giuli et al., eds., pp. 64-69 1991.
The New Yorker, Sep. 20, 1993, T. Monmaney, "Marshall's Hunch".
"Oesophageal multipurpose monitoring probe", Baker et al., Anaesthesia, 1983, vol. 38, pp. 892-897.
World Wide Patent Monocrystant . . . (Brochure).
Digestive Diseases, Reprint, vol. 8, Suppl. 1, pp. 60-70, 1990, Scarpignato et al., "Simultaneous Measurement and Recording . . . ".
Hojgaard et al., "A New Method for Measurement of the Electrical Potential Difference Across the Stomach Wall", 1991. pp. 847-858.
"Ambulatory Monitoring of Gastric Emptying", Hoeft et al., May 16, 1993, American Assoc. of the Study of Live Diseases.

*Primary Examiner*—Lee S. Cohen
*Assistant Examiner*—Robert L. Nasser, Jr.
*Attorney, Agent, or Firm*—Stephen C. Glazier

[57] ABSTRACT

The present invention teaches a method and a system for ambulatory recording of the pH and the presence of various materials in compartments of the gastro-intestinal tract. The invention also reports the pH pattern in relation to the prevalence of the materials, and analyses to which degree such materials are in active or inactive states in their normal or foreign compartments. This is useful in situations, for example, when duodenal material is refluxed into the stomach and esophagus. The invention involves a gastro-intestinal catheter with a pH sensor and a combined light absorption and fluorescence sensor, a signal recorder and processor, and a written report producer.

4 Claims, 5 Drawing Sheets

U.S. PATENT DOCUMENTS

| | | | |
|---|---|---|---|
| 3,669,095 | 6/1972 | Kobayashi et al. | |
| 3,690,309 | 9/1972 | Pluzhnikov et al. | |
| 3,817,241 | 6/1974 | Grausz. | |
| 3,905,889 | 9/1975 | Macur et al. | |
| 3,923,626 | 12/1975 | Niedrach et al. | |
| 4,016,866 | 4/1977 | Lawton. | |
| 4,063,548 | 12/1977 | Klatt et al. | |
| 4,073,287 | 2/1978 | Bradley et al. | |
| 4,119,498 | 10/1978 | Edwall et al. | |
| 4,176,659 | 12/1979 | Rolfe. | |
| 4,197,852 | 4/1980 | Schindler et al. | |
| 4,208,588 | 6/1980 | Rudin. | |
| 4,214,593 | 7/1980 | Imbruce et al. | |
| 4,265,249 | 5/1981 | Schindler et al. | 128/635 |
| 4,299,929 | 11/1981 | Sakano et al. | |
| 4,381,011 | 4/1983 | Somers, 3rd | 128/635 |
| 4,442,841 | 4/1984 | Uehara et al. | |
| 4,471,779 | 9/1984 | Antoshkiw et al. | |
| 4,476,871 | 10/1984 | Hon. | |
| 4,478,222 | 10/1984 | Koning et al. | |
| 4,486,290 | 12/1984 | Cahalan et al. | |
| 4,487,206 | 12/1984 | Aagard. | |
| 4,503,859 | 3/1985 | Petty et al. | |
| 4,508,103 | 4/1985 | Calisi. | |
| 4,577,640 | 3/1986 | Hofmeister. | |
| 4,593,701 | 6/1986 | Kobayashi et al. | |
| 4,600,015 | 7/1986 | Evans et al. | |
| 4,618,929 | 10/1986 | Miller et al. | |
| 4,631,061 | 12/1986 | Martin. | |
| 4,632,119 | 12/1986 | Reichstein. | |
| 4,642,104 | 2/1987 | Sakamoto et al. | |
| 4,655,225 | 4/1987 | Dahne et al. | 128/633 |
| 4,681,116 | 7/1987 | Settler. | |
| 4,682,596 | 7/1987 | Bales et al. | |
| 4,691,708 | 9/1987 | Kane. | |
| 4,696,672 | 9/1987 | Mochizuki et al. | |
| 4,700,709 | 10/1987 | Kraig. | |
| 4,700,799 | 10/1987 | Kawano. | |
| 4,703,757 | 11/1987 | Cohen. | |
| 4,705,503 | 11/1987 | Dorman et al. | |
| 4,729,384 | 3/1988 | Bazenet. | |
| 4,748,113 | 5/1988 | Marshall. | |
| 4,748,562 | 5/1988 | Miller | 128/635 |
| 4,757,194 | 7/1988 | Simms. | |
| 4,776,347 | 10/1988 | Matthews. | |
| 4,796,629 | 1/1989 | Grayzel. | |
| 4,803,992 | 2/1989 | Lemelson | 128/634 |
| 4,815,471 | 3/1989 | Stobie. | |
| 4,834,101 | 5/1989 | Collison et al. | |
| 4,850,371 | 7/1989 | Broadhurst et al. | |
| 4,873,990 | 10/1989 | Holmes et al. | |
| 4,887,610 | 12/1989 | Mittal. | |
| 4,892,101 | 1/1990 | Cheung et al. | 128/633 |
| 4,901,731 | 2/1990 | Millar. | |
| 4,922,919 | 5/1990 | Novack | 128/635 |
| 4,924,877 | 5/1990 | Brooks. | |
| 4,966,161 | 10/1990 | Wallace et al. | |
| 4,975,581 | 12/1990 | Robinson et al. | |
| 4,976,265 | 12/1990 | Falcial et al. | 128/634 |
| 4,981,470 | 1/1991 | Bombeck, IV. | |
| 4,986,671 | 1/1991 | Sun et al. | |
| 4,991,590 | 2/1991 | Shi. | |
| 4,996,161 | 2/1991 | Conners et al. | |
| 5,005,584 | 4/1991 | Little. | |
| 5,007,427 | 4/1991 | Suzuki et al. | |
| 5,018,529 | 5/1991 | Tenerz. | |
| 5,022,396 | 6/1991 | Watanabe. | |
| 5,025,786 | 6/1991 | Siegel. | |
| 5,046,497 | 9/1991 | Millar. | |
| 5,047,627 | 10/1991 | Yim et al. | 128/634 |
| 5,054,487 | 10/1991 | Clarke. | |
| 5,103,835 | 4/1992 | Yamada et al. | |
| 5,105,812 | 4/1992 | Corman. | |
| 5,108,364 | 4/1992 | Takezawa et al. | |
| 5,117,827 | 6/1992 | Stuebe et al. | 128/635 |
| 5,119,498 | 6/1992 | McNeill et al. | |
| 5,151,598 | 9/1992 | Denen. | |
| 5,158,083 | 10/1992 | Sacristan et al. | |
| 5,184,619 | 2/1993 | Austin. | |
| 5,199,443 | 4/1993 | Maurer et al. | |
| 5,207,226 | 5/1993 | Bailin et al. | |
| 5,222,594 | 6/1993 | Sumino. | |
| 5,280,786 | 1/1994 | Wlodarczyk et al. | 128/634 |
| 5,291,884 | 3/1994 | Heinemann et al. | 128/633 |
| 5,301,673 | 4/1994 | Rabito et al. | |
| 5,314,804 | 5/1994 | Boguslaski et al. | |

FIG. 5

PREPRANDIAL

| pH INTERVAL | % TIME PEPSIN EXP | % TIME BILIRUBIN EXP |
|---|---|---|
| pH 0.7-2.0 | 3 | 6 |
| pH 2-4 | 3 | 7 |
| pH 4-6 | 3 | 2 |
| pH 6-8 | 5 | 2 |

POSTPRANDIAL

| pH INTERVAL | % TIME PEPSIN EXP | % TIME BILIRUBIN EXP |
|---|---|---|
| pH 0.7-2.0 | X | X |
| pH 2-4 | X | X |
| pH 4-6 | X | X |
| pH 6-8 | X | X |

NOCTURNAL

| pH INTERVAL | % TIME PEPSIN EXP | % TIME BILIRUBIN EXP |
|---|---|---|
| pH 0.7-2.0 | X | X |
| pH 2-4 | X | X |
| pH 4-6 | X | X |
| pH 6-8 | X | X |

SYMPTOM

| pH INTERVAL | % TIME PEPSIN EXP | % TIME BILIRUBIN EXP |
|---|---|---|
| pH 0.7-2.0 | X | X |
| pH 2-4 | X | X |
| pH 4-6 | X | X |
| pH 6-8 | X | X |

AMBULATORY RECORDING OF THE PRESENCE AND ACTIVITY OF SUBSTANCES IN GASTRO-INTESTINAL COMPARTMENTS

BACKGROUND OF THE INVENTION

The pH and composition of fluids and materials vary in different compartments of the gastro-intestinal tract, such as the esophagus, the stomach, the duodenum, and the colon. Normally, reflux of material from one compartment to another compartment more proximal to the mouth (such as duodeno-gastric reflux or gastro-esophageal reflux) may occur on a limited basis. However, in the case of certain abnormalities and progressive diseases, reflux of material (such as secreted components, digestive components, metabolites, and white blood cells) may be more prevalent than normal. The degree to which such components may cause physical damage depends not only on pH, but also on the presence of specific ingredients such as components of bile acid and pancreatic juice. Such components may however be deleterious only in certain activated stages defined by the pH of the gastro-intestinal compartment, or the pH of the fluid that the component is in.

This invention is a method and a system (comprising a catheter, a recording device and an analysis software package) which for the first time can record on an ambulatory basis both the pH of, and presence of various substances in, the gastro-intestinal tract, and thereby ascertain if a patient is exposed to an excessive amount of agents in a deleterious active state. Substances are identified by monitoring their distinctive light absorption and fluorescence characteristics.

Ambulatory recording of pH has become a common procedure to diagnose duodeno-gastric and gastro-esophageal reflux disease. One commonly used system for this purpose is the Synectics Liberty TM System. This comprises a patented single crystal antimony pH sensor (see U.S. Pat. No. 4,119,498), a digital recorder (the Synectics Digitrapper TM), and a copyrighted software analysis package (the Synectics EsopHogram TM package). The U.S. headquarters of Synectics Medical, Inc. are at 1425 Greenway Drive, Suite 600, Irving, Tex. 75038. The world headquarters of Synectics Medical AB are at Renstiernas Gata 12, S-116 28 Stockholm, Sweden.

Current ambulatory methods of monitoring pH do not give indications of the type of components that may be included in the monitored fluid, even though, for instance, an alkaline shift in gastric pH may indicate the possible presence of refluxed bile acid.

Fiber optic recording of bilirubin in gastric juice by means of measuring the absorption of electromagnetic radiation for at least two discrete wavelengths of said radiation has been taught in U.S. Pat. No. 4,976,265 by Falcial et al. However, this patent does not describe the measurement of a continuous spectra; it does not describe the measurement of both pH and bilirubin; nor does it describe the measurement of fluorescence; and it does not describe the use of pH as a means to estimate the possibly deleterious effect of bile acid (which is active only in the pH range of 5 to 8).

Clarke described in U.S. Pat. No. 5,054,487 a system for non-invasive material analysis, especially for liquids such as blood, using an illumination source with a plurality of discrete wavelengths and measuring the intensity of reflected light. This patent fails, however, to describe any measurement of gastric juice. Nor does it describe measurements of continuous wavelengths. Nor does it describe measurements of fluorescence. Nor does it describe any combined measurement of the contents of the gastric juice and pH. Nor does it describe the method of using pH as an indicator, whether the measured components are active or not.

Robinson et al. teaches in U.S. Pat. No. 4,975,581 a "Method Of And Apparatus For Determining The Similarity Of A Biologic Analyte From A Model Constructed From Know Biological Fluids." This invention describes a preferred embodiment for noninvasive measurement of blood glucose. Robertson mentions that the device can also be used for measuring alcohol, ketoses, fatty acids, cholesterol, lipoproteins, triglycerides, while blood cells, albumin, blood urea nitrogen, creatinine, concurrent medications such as drugs and any other infrared absorptive components present in a biological analyte fluid. All of the above components indicate that Robinson is focusing on measuring blood and blood components non-invasively.

Robertson also describes an alternative embodiment where interstitial fluid (fluid in between cells) and subdermal fluids are monitored. This is clearly also for similar applications where it is thought that glucose levels should control an insulin pump in an automatic loop, something that will be of great benefits to diabetics.

it In addition, Robertson describes an embodiment in which a fiber is inserted in the blood for direct measurements and it is clear that Robinson's intention is to measure similar components as described above.

Finally, Robertson describes an embodiment where biological sample fluid in internal organs (such as the glucose dependent brain or liver) is irradiated by several wavelengths in a near-infrared spectrum; and it is also understood that in these embodiments such components will be measured. Nowhere in Robinson is it described to measure the contents of the gastro-intestinal canal, which would be a different embodiment not thought of by Robinson. Nowhere is it described to use fluorescence as a measurement technique, nor to combine spectrophotometric and fluorescence measurements in one instrument for simultaneous measurement of both absorption and fluorescence. Nowhere is it described to use sweeping pulses of continuous spectra emitted from a set of RGB, near-infrared and infrared light emitting diodes in such a way that the reflective response in addition to the fluorescence response can be scanned on a continuous basis, thus making an array of infrared to optical electrical transducers redundant. Nowhere is it mentioned to measure pH simultaneously with the prevalence of enzymatic compounds to evaluate whether they are in an active state or not.

Other efforts to measure components of gastric juice include intra-gastro-intestinal catheters with other ion specific sensors such as sodium electrodes. Said ion specific sensors may come to be used as an adjunct to the present invention, as a validation and enhancement of the findings made with the present invention.

SUMMARY OF THE INVENTION

The present invention teaches a method and a system for ambulatory recording of the pH of and the presence of various materials in compartments of the gastro-intestinal tract. The invention also reports the pH pattern in relation to the prevalence of the materials, and analyses the degree to which such materials are in active or inactive states in their normal or foreign compartments. This is useful in situations, for example, when duodenal material is refluxed into the stomach and esophagus.

The system of the present invention comprises a gastro-intestinal catheter, a modified digital recorder and an analysis software program. The catheter includes a pH sensor with or without internal reference, and with or without means for pressure measurement, potential difference measurements, impedance measurements, or other measurements, in a tube made of silicon. The catheter also includes one efferent bundle of optical fibers, and one afferent bundle of optical fibers, with a gap between the adjacent distal ends of the two bundles, and a sensing reflection head in the gap at the distal end of the catheter. The distal end of the catheter is inserted into the sample material to be monitored in a gastro-intestinal compartment, and the monitored material enters the gap. Light is passed through the material from the efferent bundle. The reflected light is collected, together with any fluorescence from the material by the afferent bundle. The light absorption and fluorescence of the monitored material is characteristic of the material's identity and state of activity.

The catheter is connected to a Holter pH recorder into which a combined spectrophotometer and a fluorescence meter is built in. This operates by means of an illumination source, said source comprising a set of RGB (red, green and blue), near-infrared and infrared light emitting diodes, said source controlled by timer and microprocessor circuits in such a way that said source emits light pulses, each pulse comprising sweeping continuous electromagnetic spectra in frequencies and patterns controlled by the microprocessor. The light pulses may or may not pass through a polarizing fiber before entering the efferent catheter fiber bundle and passing into the gap of said catheter. The distal end of the catheter is inserted into the fluid in a gastro-intestinal compartment so that the fluid to be studied is in said gap. The light passes through the fluid to a reflection cap in the reflection head, and then back through the fluid to the afferent fiber bundle. Any fluorescent light from the fluid directly enters the fluid to the afferent fiber bundle, or reflects off the reflection cap to the afferent bundle.

The Digitrapper then receives the reflected light and any fluorescent light through a built-in sensor sensitive to electromagnetic radiation capable of detecting both reflected and fluorescence wavelength and intensities on a continuous basis. Both emitted and received signals are converted from analog to digital ("AD converted") and stored in the digital memory of the recorder.

The Holter recorder further comprises means for measuring pH which can be used to determine the state of activity of the spectrometrically and fluorescently monitored substances.

In some applications where a polarized filter is used an external electrical field may be used for depolarization and orientation of compounds.

The patient is thus intubated with only one catheter and is free to go about his daily routine in his normal environment while wearing the combined ambulatory pH, spectrophotometer and fluorescent measurement Digitrapper. When the recording is done the patient returns the Digitrapper and the catheter, and the recorded data is analyzed either inside the recorder or by an external device such as a computer. The analysis software reports pH levels and the prevalence of various substances during various periods of a 24 cycle and during symptoms, in such a way that the degree of activity of the substances are described.

The analysis software analyzes the pH values. The software also determines the identity and concentration of the substances. It does this by analyzing the observed light absorption and fluorescent characteristics of the monitored substances, looking for the distinctive light absorption and fluorescent characteristics of various possible human gastro-intestinal contents and mixtures, and relating them to the pH values.

This enables for the first time an ambulatory procedure where pH values and the state of activity of the substances, and their patterns of exposure to various compartments of the gastro-intestinal tract, can be evaluated.

BRIEF DESCRIPTION OF THE DRAWINGS

FIG. 4 and FIG. 5 illustrate a sample of the software generated report constructed in accordance with the principles of the invention.

DETAILED DESCRIPTION

Figure 1:
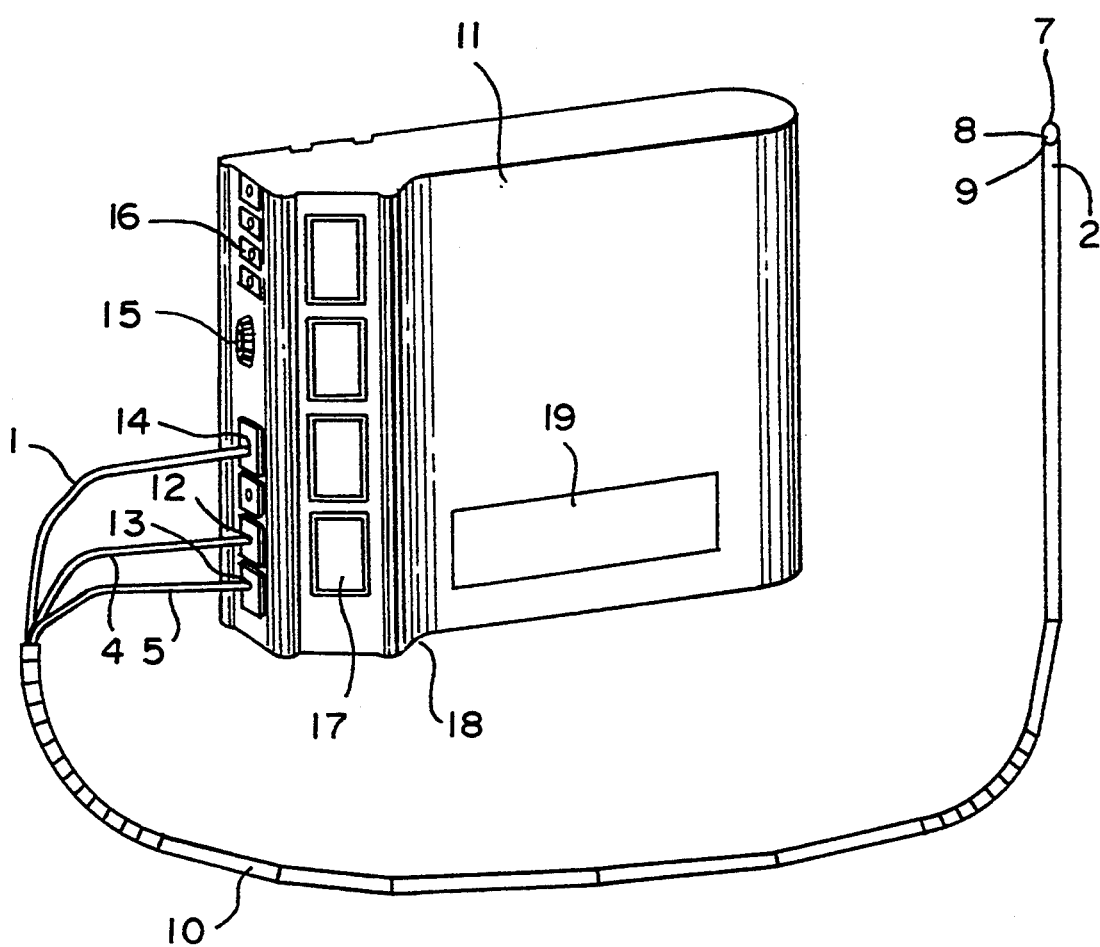
FIG. 1 illustrates the external appearance of the system comprising the catheter, the combined ambulatory pH and spectrophotometer recorder.

FIG. 1 shows one possible realization of the system in accordance to the principles of the invention. A pH catheter lead (1) with pH sensor (2) is combined with efferent (4) and afferent (5) fiberoptic bundles to an absorption and fluorescence sensor (6) comprising a reflector (7) (which may not be necessary if only fluorescence is to be measured), held in place by a double wired steel wire (8) at a distance from the optic fibers thus creating a gap or space (9) into which gastric juice may freely move. The catheter (10) is connected to a battery powered Digitrapper recorder (11) by means of optical connectors (12) and (13) (for the optical part of the catheter) and by means of electrical connector (14) (for the pH part of the catheter). The Digitrapper includes further one fifteen polar D-sub connector (15) for parallel communication including downloading and uploading of data to computers and printers and one optic connector (16) for patient isolated on-line connection with similar devices.

The Digitrapper (11) receives measured spectrophotometric and/or fluorescence and pH data and stores such data in random access memory (RAM). The Digitrapper (11) includes further a set of four switches (17) used first for the set up of the instrument and then as patient event keys during the recording of the data. The Digitrapper (11) is switched on and off with switch (18). The display (19) instructs the user during the set up procedures for the Digitrapper and indicates the time and event mode during recording. The catheter (10) is introduced into the gastrointestinal tract and properly positioned with sensors located in the places in the gastro-intestinal tract that are to be studied. The patient is then free to move around with the catheter (10) connected to Digitrapper (11) which is worn by the patient.

When the recording is completed the data is transferred to a printer or a computer by means of connector (15) in order to generate a report (20).

Figure 2:
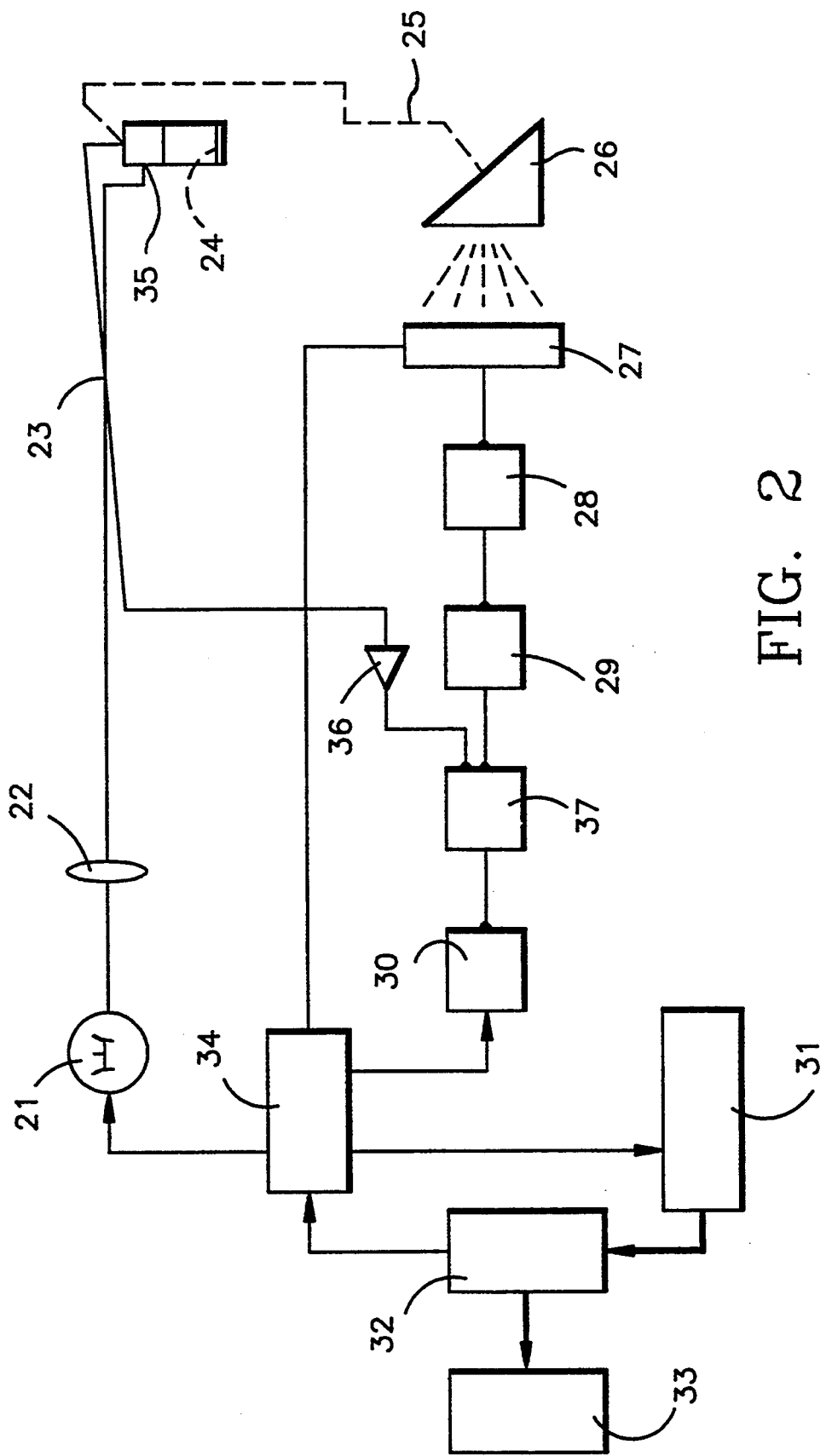
FIG. 2 is a block diagram illustrating an ambulatory device constructed in accordance with the principles of the invention.

FIG. 2 illustrates a schematic block diagram in accordance with the principles of the invention. A light source (21) comprising a set of RGB, near-infrared and infrared light emitting diodes (controlled by timing unit (34) and a microprocessor CPU (32)) emits a sweeping continuous light pulse every eight seconds through lens (22) that focuses the emitted beams into the efferent fiber bundle (23). The light pulse travels through the efferent fiber bundle (23) to and through the study sample, such as gastric juice. Then the light pulse is reflected by reflector (24) into afferent fiber bundle (25). The reflected light pulse travels together with any fluorescence light through prism (26) to a sensor (27) sensitive to continuous electromagnetic radiation. The resulting signals are amplified by amplifier (28) and filtered by filter (29) and led via an analog multiplexer (37) to sample and hold circuit (30), after which timer (34) may switch off the light emitting source (21). Then the sample and hold circuit (30) signals are shifted to an 8-bit analog to digital converter ("AD-converter") (31) which downloads the now digital signals into random access memory ("RAM") (33) via interrupts to the microprocessor CPU (32). A pH sensor (35) mounted on the catheter that includes the fiber optic bundles (23) and (25) is connected to pH amplifier (36) by an electrical lead in the catheter. The amplifier (36) sends analog pH signals via analog multiplexer (37). The signals from multiplexer (37) take the same path as the spectrophotometric signals.

Synchronization of measurements is handled by the timing unit (34) and microprocessor (32) which control light emission. As the emitted light sweeps through its wavelengths, this synchronization correlates each wavelength of emitted light with the intensity and wavelengths of the resulting reflected and fluorescent light that is received by the afferent bundle. This indicates absorption and fluorescence which in turn indicates the presence of specific materials. This data and analysis is also correlated with pH.

Figure 3:
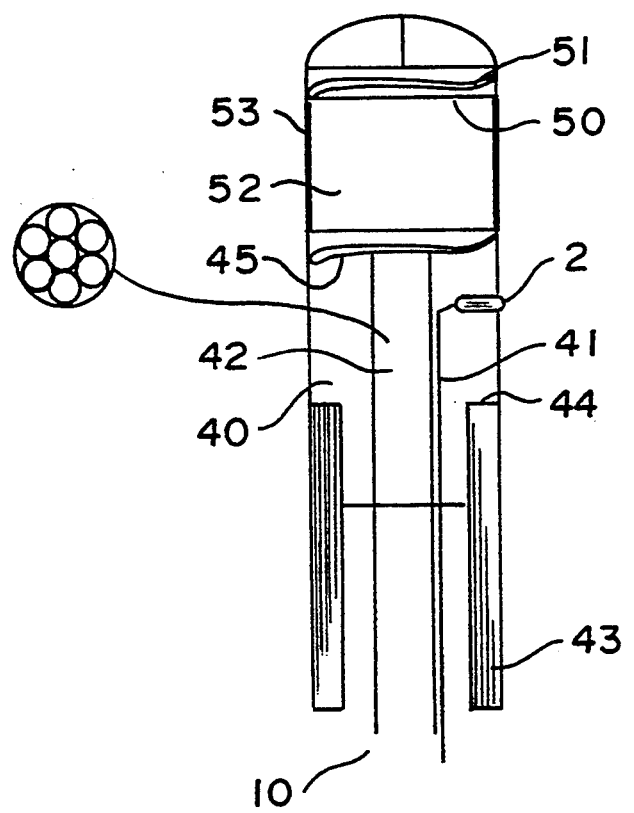
FIG. 3 illustrates the combined pH and spectrophotometer fiberoptic catheter in accordance with the principles of the invention.

FIG. 3 is a schematic illustration of the distal sensing part of the catheter (10). pH sensor (2) is mounted in head (40) and via lead (41) connected to the proximal part of catheter (10) ending with a connector to the Digitrapper recorder. The head (40) is made of polycarbonate and includes a channel (42) through which afferent and efferent fiber bundles pass to the distal end of said head. A 3.0 mm outer diameter PVC tube (43) is fastened to the proximal part of head (40) by means of a neck (44) in said head. The distal end of head (40) is glued to prevent leakage of fluids around the fibers through channel (42) in head (40) into catheter body (10). The distal end of head (40) is polished to remove glue and give the fibers a smooth surface. The mantle surface of the distal end of head (40) has winds (45) on to which reflector (50) is attached by means of two split double springs (51). This leaves an empty space or gap (52) between the reflector (50) and the distal part of head (40) in which the studied material, such as gastric juice, may freely pass. Reflector (50) is held in position by the two split wires (53) of two split double springs (51).

Figure 4:
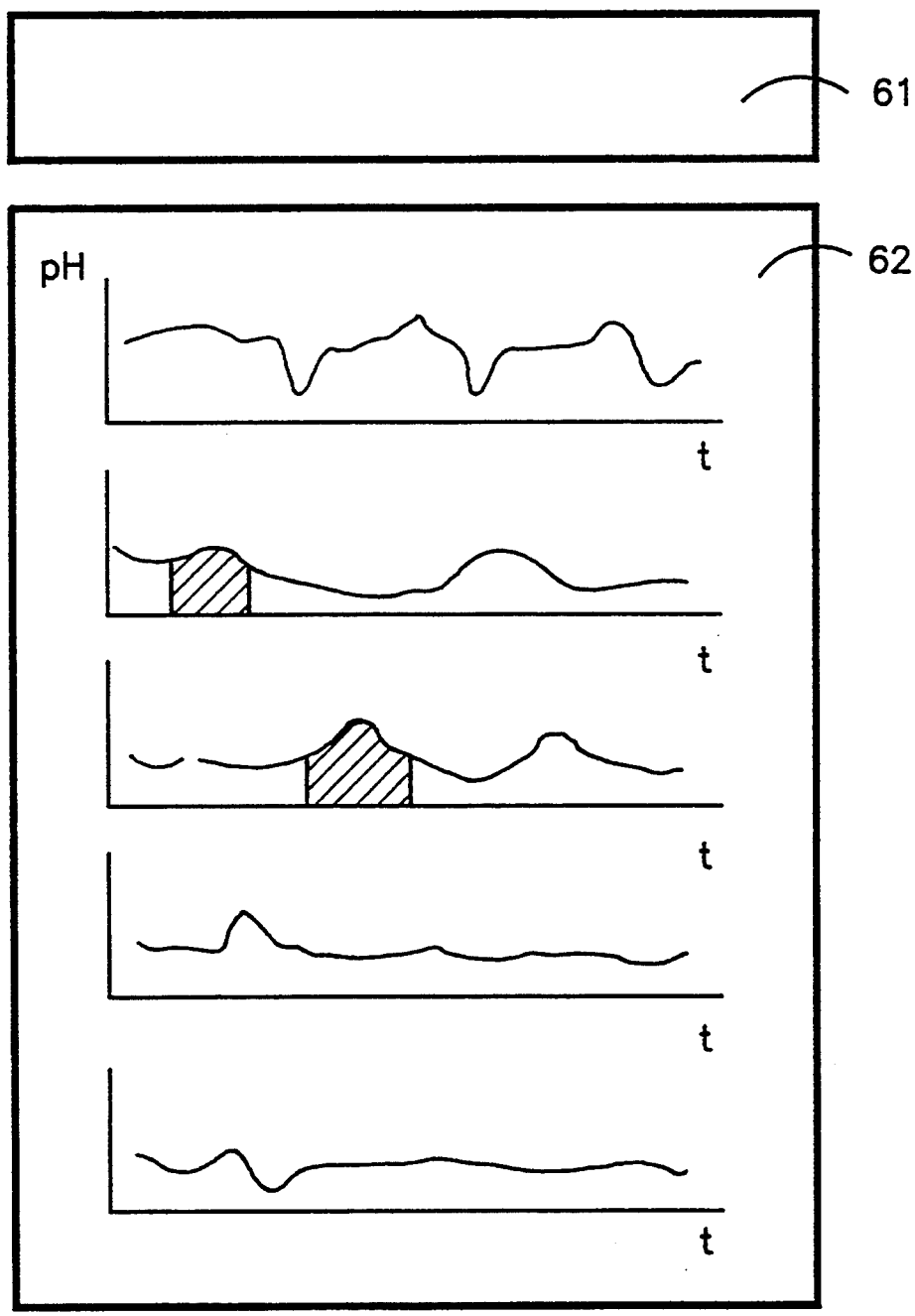

FIG. 4 illustrates one part of an analysis report as it may be printed after the recorded data is analyzed by the analysis software. The top part of the report (61) is used for patient demographic data, information about who is performing the procedure, and why the procedure is being performed. The second part (62) is a graphic part where pH and absorption curves of various substances are plotted against time. As various substances are active at different pH intervals, the time during which each substance is active is marked by shadowing the area under or over a certain level on the active parts of the graphs.

The third part (63) of the report is in table form as shown in FIG. 5. In such tables pH analysis data and spectrophotometric data are combined so that the percentage time exposure of a substance in an active deleterious state is reported for various periods of the 24 hours such as total time, preprandial and postprandial and meal periods, supine and upright periods, and various symptomatic periods. The tables part of the report may or may not include a standard 24 hour pH table such as generated by the EsopHogram TM software.

Similar tables can be developed in the report to correlate the pH data, the spectrophotometer data, and the fluorescent data, together with the indications of the spectrophotometric data and the fluorescent data as to the presence and state of activity of materials in the gastro-intestinal compartments monitored by the distal end of the catheter.

The software identifies the materials present by analyzing the light absorption and fluorescent data. Light absorption data is analyzed for the characteristic light absorption patterns of possible gastro-intestinal contents. Likewise, fluorescent data is analyzed for the characteristic fluorescent patterns, indicating the presence of specific materials. After the analysis, the software prints a written report showing the correlation of time, pH data, and indicated materials present. This information can be presented in graphic and tabular form, and otherwise.

The embodiments illustrated and discussed in the specification are intended only to teach those skilled in the art the best way known by the inventors to make and use this invention. Nothing in the specification should be considered as limiting the scope of the present invention. Many changes could be made by those skilled in the art to produce equivalent systems without departing from the invention. The present invention should be limited only by the following claims and their legal equivalents.

I claim:

1. A gastro-intestinal catheter comprising:
   (a) a catheter with a tubular body, a proximal end, a distal end, an interior, an exterior, and a head section at the distal end,
   (b) a means for sensing pH that extends through the interior of the body, and
   (c) a means for sensing light absorption and fluorescence by gastro-intestinal contents, this means for sensing light extending through the interior of the body, and communicating to the exterior of the body at or near the distal end of the body, the means for sensing light absorption and fluorescence further comprising:
   (d) a light absorption and fluorensence sensor mounted in the head section, comprising means for sensing light absorption and fluorescence by gastro-intestinal contents,
   (e) an efferent fiberoptic bundle communicating from the proximal end of the body, through the interior of the body, to the light absorption and fluorescence sensor, and
   (f) an efferent fiberoptic bundle communicating from the light absorption and fluorescence sensor through the interior of the body, to the proximal end of the body, the light absorption and fluorescence sensor further comprising:

(g) a reflector, with a proximal surface and a distal surface, the reflector attached to the distal end of the body by two wires and two springs such that an open space remains between the attached reflector and the distal end of the body, with a proximal end of each wire attached to the distal end of the body and a distal end of each wire attached to the reflector and the two springs attached to the distal ends of the wires and the springs running across the distal surface of the reflector.

2. An apparatus for producing a written report about ambulatory recorded data regarding the presence and activity of substances in gastro-intestinal compartments, comprising:

(a) means for reading ambulatory recorded light absorption data, fluorescence data, time data and pH data, (b) means for analyzing the light absorption data for characteristic light absorption patterns of possible gastro-intestinal materials, and identifying a material present, (c) means for analyzing the fluorescence data for characteristic fluorescence patterns of possible gastro-intestinal materials, and identifying a material present, and (d) means for printing a written report showing the correlation between the time data, the pH data, and the identified materials present.

3. The invention in claim 2, further comprising:

(a) means for analyzing the pH data and correlating it with the light absorption data, fluorescence data, and the material present, and (b) means for analyzing the time data and correlating it with the light absorption data, fluorescence data, and the material present.

4. A method for using an electronic computer to produce a written report about ambulatory recorded data about the presence and activity of substances in gastro-intestinal compartments, comprising:

(a) reading ambulatory recorded light absorption data, fluorescence data, time data and pH data, (b) analyzing the light absorption data for characteristic light absorption patterns of possible gastro-intestinal materials, and identifying a material present, (c) analyzing the fluorescence data for characteristic fluorescence patterns of possible gastro-intestinal materials, and identifying materials present, and (d) printing a written report showing the correlation between the time data, the pH data, and the identified materials present.

* * * * *